United States Patent [19]

Morgan et al.

[11] 4,442,214

[45] Apr. 10, 1984

[54] THERMO-STABLE MICRO-ORGANISM

[75] Inventors: Hugh W. Morgan; Roy M. Daniel, both of Hamilton, New Zealand

[73] Assignee: Development Finance Corporation of New Zealand, Wellington, New Zealand

[21] Appl. No.: 176,528

[22] Filed: Aug. 8, 1980

[30] Foreign Application Priority Data

Aug. 8, 1979 [NZ] New Zealand .................. 191246

[51] Int. Cl.$^3$ .................. C12N 1/20; C12N 9/50
[52] U.S. Cl. .................. 435/253; 435/219
[58] Field of Search .................. 435/212, 220–222, 435/253, 822

[56] References Cited

U.S. PATENT DOCUMENTS

| | | | |
|---|---|---|---|
| 3,713,983 | 1/1973 | Yokotsuka et al. | 435/219 |
| 3,796,635 | 3/1974 | Delente | 435/221 |
| 3,871,963 | 3/1975 | Tobe et al. | 435/221 |
| 3,953,296 | 7/1974 | Trutnovsky et al. | 435/14 |
| 4,100,028 | 7/1978 | Mikhailovich et al. | 435/815 |

FOREIGN PATENT DOCUMENTS 54-132295 10/1979 Japan .................. 435/822

OTHER PUBLICATIONS

Hickey, et al., The Electron Transport System of an Extremely Thermophilic Bacterium, *Journal of General Microbiology*, vol. 114, 1979, pp. 195–200.
Brock, et al., Thermus aquaticus gen. n. and sp. n., a Nonsporulating Extreme Thermophile, *Journal of Bacteriology*, vol. 98, 1969, pp. 289–297.
Degryse et al., A Comparative Analysis of Extreme Thermophilic Bacteria Belonging to the Genus Thermus, *Chem. Abs.*, vol. 89, 1978, p. 420.
Chemical Abstracts, vol. 76, 110112q.
Chemical Abstracts, vol. 89, 103613u.
Chemical Abstracts, vol. 89, 19867x.
Chemical Abstracts, vol. 88, 18736w.
Chemical Abstracts, vol. 80, 142970s.
Chemical Abstracts, vol. 79, 1837w.
Chemical Abstracts, vol. 78, 55147u.
Chemical Abstracts, vol. 83, 174382e.
Chemical Abstracts, vol. 75, 95656d.
Chemical Abstracts, vol. 70, 103992z.
Gillespie, D., Syrup: A New By-Product of Milk, *Scottish Farmer*, 11/22/77.
Zaborsky, O. R., *Immobilized Enzymes*, CRC Press, 1973, p. 37.

*Primary Examiner*—Albert T. Meyers
*Assistant Examiner*—Kathleen S. McCowin
*Attorney, Agent, or Firm*—Murray and Whisenhunt

[57] ABSTRACT

The invention relates to an extremely thermophilic bacterium, THERMUS T-351, and a thermophilic protease, CALDOLYSIN, derived therefrom. The bacterium cells are Gram negative, non-sporulating rods. Its natural environment is a hot pool at 79°±4° C. The protease is stable at temperatures up to 75° C. at a pH range of 4 to 12. It is most active at temperatures of 65° C. to 85° C. but retains at least some activity at lower temperatures.

14 Claims, No Drawings

THERMO-STABLE MICRO-ORGANISM

FIELD OF THE INVENTION

This invention relates to a novel micro-organism capable of producing a thermostable extracellular proteolytic enzyme. It also relates to the method of preparing the proteolytic enzyme and to the proteolytic enzyme itself.

SUMMARY OF THE INVENTION

It is recognised that there is a demand for thermostable proteolytic enzymes in the food, fermentation, animal feed and pharmaceutical industries which is not being entirely met. The inventors have succeeded in isolating a micro-organism from a hot pool in the thermal area of Rotorua, New Zealand, which organism is capable of producing a thermostable proteolytic enzyme.

It is an object of this invention to provide starting material capable of producing a thermostable proteolytic enzyme and to provide a proteolytic enzyme which goes some way towards meeting the aforementioned demand or at least provides the public with a useful choice.

Accordingly the invention may be said broadly to consist in THERMUS T-351 (as herein defined) in a substantially biologically pure form.

In another aspect the invention may be said broadly to consist in a process for isolating THERMUS T-351 which comprises isolating a sample of solution from a hot pool (at 79°±4° C.) low in sulphide at pH 7.8 containing said micro-organism, preparing a culture from said sample and maintaining said culture at a temperature of 65° C. to 85° C. and a pH between 7.2 and 8.2 for a time sufficient to produce an adequate yield and isolating the THERMUS T-351 from said culture during the late log phase thereof.

In another aspect the invention may be said broadly to consist in THERMUS T-351 whenever prepared by the foregoing process.

In another aspect the invention may be said to consist in CALDOLYSIN (as herein defined) in a substantially pure form.

In another aspect the invention may be said broadly to consist in a method of preparing CALDOLYSIN (as herein defined) which comprises centrifuging a culture of THERMUS T-351, subjecting the supernatant from said centrifugation to affinity chromatography on a suitable activated affinity chromatography gel and eluting the CALDOLYSIN from said gel with a suitable buffer.

In another aspect the invention may be said to consist in CALDOLYSIN (as herein defined) whenever prepared by the process hereinbefore defined.

In another aspect the invention may be said broadly to consist in CALDOLYSIN (as herein defined) immobilised on a suitable substrate.

DETAILED DESCRIPTION OF THE INVENTION

The invention consists in the foregoing and also envisages constructions of which the following gives examples.

DEFINITIONS

1. THERMUS T-351

This micro-organism was isolated from Hot Pool No. 351 as marked on the map of "Whakarewarewa Hot Springs", 1:2000, 1st Edition by New Zealand Geological Survey (Bibliographic reference-Lloyd, E. F. 1974, Geology of Whakarewarewa hot springs, DSIR information series No. 104 DSIR, Wellington, N.Z.). The hot pool was at (79°±4° C.), was low in sulphide, at pH 7.5 to 7.8. It grew poorly below 60° C. It was obligately aerobic. The cells were Gram negative, non-motile, non-sporulating rods. It is similar to THERMUS AQUATICUS (Brock et al., *J. Bacteriol* 98, 289–287; Degryse et al, *Archives of Microbiology* 117, 18) but the inventors have noted a significant difference in cytochrome composition of between THERMUS-351 and THERMUS AQUATICUS. The product exhibits optimal activity at 70° to 80° C. and negligible activity below 40° C. Other properties of this microorganism are set out herein below and are also described in Hickey and Daniel, *J. of Gen. Microbiology* (1979), 114, 195–200, the text of which is hereby incorporated by reference.

2. CALDOLYSIN

This is a proteolytic enzyme produced by THERMUS T-351 and isolated by the process described below. It is a protease having molecular weight 20,000±3,000. It has an isoelectric point of approximately 8.5 and its enzymatic activity is described below. This enzyme is stable at temperatures of 75° C. and below, in the presence of divalent cations, particularly calcium ions. It is stable at pH values from 4 to 12 in the presence of calcium ions. Other properties and the method of preparation of this product are set out herein below.

EXAMPLE 1a

Isolation of THERMUS T-351

Samples were taken from the hot pool identified under the definition of THERMUS T-351 herein above. Isolation was carried out by repeated sub-culturing at 75° C. of the organisms contained in a 1 ml sample from the hot pool, in 10 ml of half strength nutrient broth, pH 8.0. This was followed by growth in the medium described in example 1b (i).

EXAMPLE 1b

Cultivation of THERMUS T-351

(i) Cultures were maintained on a medium consisting of Allen's salts, (Jackson et al., *Archiv. fur Mikrobiol* 88, 127–133), with 0.1% w/v yeast extract (BBL) and 0.1% w/v trypticase (BBL) in liquid culture at 75° C. The medium was adjusted to pH 8.2 prior to autoclaving. The final pH was 7.5.

(ii) The organism was grown at 75° C. on a similar medium but with 0.3% yeast extract and 0.3% trypticase. 500 ml batches were grown in 2 l Erlenmeyer flasks in an orbital incubator, and either harvested for use, or used to inoculate a 20 l fermentor. The organism grow well at 75° C. under the conditions (i) and (ii) and poorly below 60° C. Cells were harvested during late log phase (10–12 hours after inoculation) at an absorbance of about 1.4 at 650 nm (about $2.5 \times 10^7$ cells ml$^{-1}$)

1c. Preparation of subcellular fractions

Cell fractions were prepared as described by Daniel (*Biochem et Biophys Acta* 216, 328–341) except that the sedimentation of small particles was carried out at 250,000 g for 1 hour.

1d. Measurement of oxidase system activities

Oxygen uptake was measured polarographically using a Rank electrode (Rank Brothers, Bottisham, Cambridge, England). The reaction mixture consisted of 0.1 M $KH_2PO_4/Na_2HPO_4$ buffer pH 7.0, a suitable amount of membrane particle protein, 50 μmol of substrate (except in the case of NADH were 5 μmol were used), in a final volume of 2.5 ml.

Buffers were equilibrated at the desired temperature with sparged air for 30 minutes.

Particles were equilibrated in the electrode for 2 minutes prior to measurement of oxygen uptake. Rates were measured over the first minute.

1e. Spectrophotometry

Difference spectra were obtained at room temperature with a Cary model 17 recording spectrophotometer.

The concentration of individual cytochromes was determined from the dithionate-reduced minus oxidised difference spectra, and for cytochrome from the reduced minus reduced +CO difference spectra, using the following wavelength pairs and extinction coefficients: c-type cytochrome, 553–540, $\epsilon_{mM}=19$ mM$^{-1}$ cm$^{-1}$ (Chance et al J. Bio.Chem. 217 439–451) total b-type cytochrome, 569–575 nm, $\epsilon_{mM}=17.5$ mM$^{-1}$cm$^{-1}$ (Deeb & Hanger (J.Bio. Chem. 239, 1024–1031); cytochrome o-CO, 417–429, $\epsilon_{mM}=170$ mM$^{-1}$cm$^{-1}$ (Daniel, (Biochem et Biophys. Acta 216, 328–341); a-type cytochrome, 602–630 and 613–630 $\epsilon_{mM}=24$ mM$^{-1}$ cm$^{-1}$ (Van Galder, (Biochem. et Biophys. Acta 118, 36–46).

Washed membrane particles were able to oxidise other substrates including glutamate and malate [>0.05 μmol $O_2$ min$^{-1}$(mg protein)$^{-1}$], and lactate, citrate, fumerate, glycerol and glucose [0.005–0.02 μmol $O_2$ min$^{-1}$(mg protein)$^{-1}$]. Except in the case of succinate and lactate, activities were enhanced by added supernatant and by NADH. Acetate, sucrose, mannitol and ethanol were not oxidised.

Both NADH and succinate oxidases had maximum activity at pH 7.0, and at a phosphate buffer molarity of 0.1 M, as determined at 75° C.

The activities of NADH and succinate oxidases were determined after 2 minutes preincubation at temperatures between 40° C. and 95° C. Each was highest at 75° C. in cell free extract and in large and small particles. The NADH oxidase rate in respiratory particles was particularly temperature sensitive, the rates at 70° C. and 80° C. being about half that at 75° C. In all cases activity at 75° C. was at least 10-fold greater than that at 40° C.

At 75° C., apart from an initial partial loss of activity the respiratory chain in whole cells, cell free extracts and respiratory particles was relatively stable, but there was a substantial short term increase in succinate respiration of whole cells and endogenous respiration followed a similar pattern. At 90° C. this was found for whole cells and cell free extracts, but not washed respiratory particles. At 90° C. the succinate oxidase of whole cells and the NADH oxides of washed respiratory particles were substantially less stable than the oxidase activities of cell free extract.

These stabilities are appreciably greater than those reported for NADH oxadase from Bacillus stearothermophilus protoplasts (Wisdom & Walker, (J. Bacteriol. 114 1336–1345).

The thermostability of the NADH oxidase activity of respiratory particles at 90° C. over a 15 minute period was unaffected by phosphate buffer concentration (0.01 M to 2.0 M), 1.0 M-$MgSO_4$ or by 10 mg ml$^{-1}$ casein. Stability was enhanced about 2-fold by 50% (v/v) glycerol, 2.0 M-$(NH_4)_2SO_4$, and 10 mg ml$^{-1}$ NADH. Rates were determined at 75° C.

Absorption peaks of a, b, and c-type cytochromes in washed respiratory particles at 613 and 602, 559 and 555 nm respectively were recorded. The major a-type cytochrome had an absorption peak at 613 nm, which is unusual: the troughs at 615 and 444 nm in the carbon monoxide spectra suggest that at least one of the a-type cytochromes is a terminal oxidase. The trough at 561 nm and the peak at 417 nm indicate the presence of cytochrome o, and the trough at 550 nm suggests that there was some CO-reactive c-type cytochrome in the respiratory particles. The high speed supernatant contained at least two soluble c-type ctyochromes since the ratio of the peaks at 420 and 426 nm varies somewhat between preparations, and at least one of these was CO-reactive.

b and c-type cytochromes in the THERMUS NH have been reported by Pask-Hughes & Williams (Scientific Progress at Oxford 62, 373–393) and a-605 and b and c-type cytochromes in a THERMUS AQUATICUS type organism by McFetters and Ulrich (J. Bacterial 110(2), 777–779).

Cytochrome concentrations [μmol cytochrome (g. pro-tein)$^{-1}$] in respiratory particles were a-602, 0.03; a-613, 0.06; total b-type, 0.89; o-0.21; total c-type 0.64: In the supernatant, c-type 0.79; CO-reactive cytochrome c, 0.02. These concentrations are fairly typical of these found in other aeorobes.

All inhibitors tested produced levels of inhibition within the range of those found in other bacteria and there was no evidence that active sites were less exposed than in non-thermophiles. Terminal oxidase inhibitors affected NADH and succinate oxidases equally, as did amytal. Rotenone had more effect on the NADH oxidase, while Bathophenanthroline 2-heptyl-4-hydroxyquinoline-N-oxide and antimycin A were all more effective inhibitors of succinate oxidase.

EXAMPLE 2a

Two Step CALDOLYSIN Purification

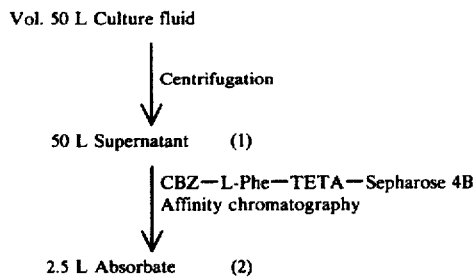

The culture fluid treated according to the flow scheme set up hereinabove comes from Example 1b. The centrifugation is conducted in a continuous flow centrifuge at 27,000 g. The pH of the Supernatant was adjusted to pH 8 prior to its being passed through the affinity gel.

TABLE 3

| STEP | | Volume (l.) | [Protein] (µg/ml) | Activity (PU/ml) | Specific Activity (PU/mg) | Purification (fold) | Yield (%) |
|---|---|---|---|---|---|---|---|
| 1. | Supernatant | 20 | 24 | .005 | .25 | 1.0 | 100 |
| 2. | Affinity Purified | 1.1 | 14 | .079 | 5.76 | 23.2 | 73 |

The experimental data set out in Table 1 herein below.

EXAMPLE 2b

Multistep Caldolysin Purification

The overall reaction scheme is set out in the following flow sheet.

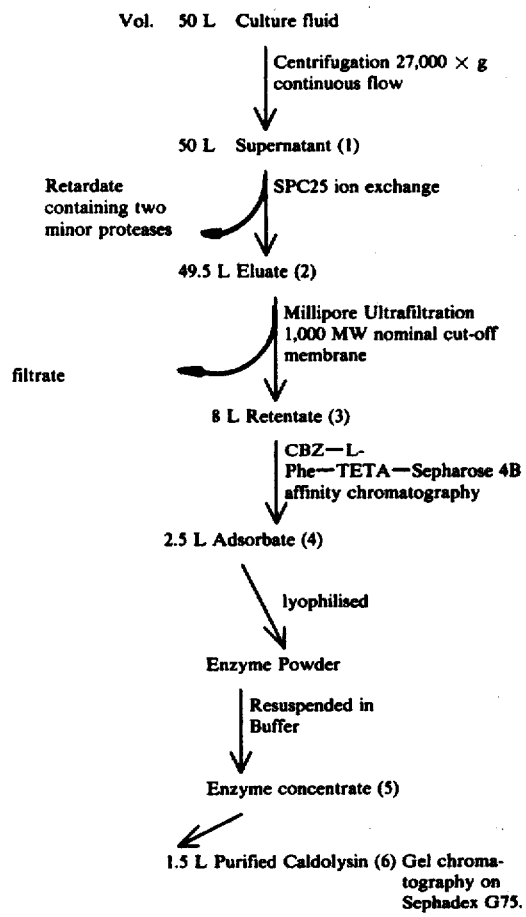

The majority of the details are set out on the accompanying flow sheet. However the ultrafiltration step concentrated the eluate (2) ten times. The retentate (3) subjected to affinity chromatography was adjusted to pH 8. the absorbate 4 was eluted as a single peak with pH 2.7 0.1 M acetic acid containing 10 mM $Ca^{2+}$.

The enzyme concentrate (5) was eluted from the G75 gel column using an eluting buffer at pH 8.1 and 10 mM $Ca^{2+}$.

The data of the various steps in the reaction scheme are set out herein below in table 2.

TABLE 2

| Step | Vol. (L) | Total protein (mg) | Total activity Proteolytic Units* (× 1000) | Sp. Act PU/mg | Yield % | Purification |
|---|---|---|---|---|---|---|
| 1. Supernatant | 50 | 4000 | 5.9 | 1.23 | 100 | 1.0 |
| 2. SPC25 Eluate | 49.5 | 2740 | 4.03 | 1.47 | 68.3 | 1.2 |
| 3. Millipore concentrate | 8 | 1410 | 3.47 | 2.46 | 58.8 | 2.0 |
| 4. Affinity purified enz. | 2.5 | 36 | 1.67 | 46.4 | 28.3 | 37.7 |
| 5. Lyophilisate conc. | 0.3 | 36 | 1.23 | 34.2 | 20.8 | 27.8 |
| 6. G75 purified enz. | 1.5 | 8.75 | 0.97 | 110.9 | 16.4 | 90.2(fold) |

*1 PU = mg tyrosine/min at 75° C., substrate 0.5% casein (Hammersten)

EXAMPLE 3

Properties of CALDOLYSIN

A. Physical (1) A Molecular weight of 20,000±3,000 was determined by gel chromatography, SDS electrophoresis, and Gradipore electrophoresis.

(2) Isoelectric point: 8.5±0.5.

(3) Response to inhibitors (Table 3) and enzymatic specificity indicate that CALDOLYSIN is as a metal-chelator-sensitive lytic protease (see Morihara (1974): "Comparative Specificity of Microbial Proteases", *Advances in Enzymology* 41, 179) with an active sight serine residue.

B. Enzymatic

CALDOLYSIN hydrolyses a range of high molecular weight protein substrates (Table 4) and some low molecular weight peptide substrates (Table 5). However, a number of common peptide analogues (protease substrates) are not hydrolysed (Table 5).

CALDOLYSIN lyses a broad range of Gram-negative bacteria, but few gram-positive microorganisms (Table 6).

C. Stability (1) Thermostability.

In the presence of 10 mM $Ca^{2+}$, 100% activity is retained at temperatures of 75° C. and below for an extended period (no loss over 170 hours). Removal of $Ca^{2+}$ markedly reduces thermostability. Half-life data at temperatures between 75° C. and 95° C. are shown in Table 4, together with published data on other thermophilic proteases.

(2) pH/Stability

CALDOLYSIN is stable (in the presence of calcium ions at 20° C.) for protracted periods at pH values of 4.0 to 12.0. At pH 3.0 $T^{\frac{1}{2}}=2$ hours.

At high and low pH values (for example pH 4 and pH 10), incubation at elevated temperatures results in a marked reduction in stability.

TABLE 3
INHIBITORS

| Type of Action | Inhibitor | Concentration | | % Inhibitor of Activity |
|---|---|---|---|---|
| General Metal Chelator | EDTA | 12.5 | mM | 100% |
| | EDTA | 10 | mM | 70% |
| | EDTA | 1 | mM | 40% |
| | EDTA | 0.13 | mM | — |
| Cysteine - Enzyme Inhibitor | Iodoacetic acid | 10 | mM | 60% |
| | " | 2 | mM | — |
| | " | 0.25 | mM | — |
| Serine - Enzyme Inhibitor | Phenylmethyl Sulfonyl Fluoride | 10 | mM | 10% |
| | | 1 | mM | — |
| | " | 5 | mM | — |
| Cysteine - Enzyme Inhibitor | p-chloromercuri benzoate | 5 | mM | — |
| | | 2.5 | mM | — |
| Zn—specific Chelator | o-phenanthroline | 10 | mM | — |
| | " | 1 | mM | — |
| Ca—specific Chelator | EGTA | 10 | mM | 45% |
| | EGTA | 1 | mM | 18% |
| | Trypsin inhibitor | 1.0 | Mg ml$^{-1}$ | — |
| Acid protease inhibitor | N—α-p-tosyl-L-lysine Chloromethyl ketone HCl | $3 \times 10^{-2}$ | mM | — |

Although the reasons are not fully understood and we do not wish to be bound by any one theory, the apparent inhibition of CALDOLYSIN by EDTA and EGTA is likely as the result of destabilisation caused by calcium removal, and the subsequent loss of enzyme activity as the result of autolysis.

TABLE 4
HYDROLYSIS OF PROTEINS BY CALDOLYSIN

| Substrate | Rate of hydrolysis ($\Delta_{280}$ min$^{-1}$ × 10$^3$) | % of rate of casein hydrolysis |
|---|---|---|
| casein | 3.33 | 100 |
| ovalbumin | 1.45 | 44 |
| bovine serum albumin | 1.33 | 40 |
| haemoglobin | 0.90 | 27 |
| collagen | 0.70 | 21 |
| fibrin | 0.65 | 18 |

| | Rate of hydrolysis ($\Delta_{440}$ min$^{-1}$ × 10$^3$) | % of rate of azo-casein hydrolysis |
|---|---|---|
| azo-casein | 2.75 | 100 |
| azo-albumin | 4.15 | 151 |
| azo-collagen | 0.87 | 32 |

| | ($\Delta A_{395}$ min$^{-1}$ × 10$^3$) | |
|---|---|---|
| elastin-congo red | 0.25 | approx. 7 |

TABLE 5
HYDROLYSIS OF PEPTIDE AND PEPTIDE ANALOGUES BY CALDOLYSIN

| Substrate | Hydrolysis | Bond hydrolysed |
|---|---|---|
| Gly—gly | — | — |
| Gly—gly—gly | — | — |
| Gly—gly—gly—gly | — | gly—gly |
| Gly—gly—gly—gly—gly | — | gly—gly |
| D-leu—gly | — | — |
| L-leu—gly | — | — |
| BOC—ala—try—met—asp—phe—NH$_2$ | — | — |
| CBZ—gly—phe—NH$_2$ | — | — |
| Acetyl—ala—ala—ala—OMe | — | ala—ala |
| CBZ—gly—pro—gly—pro—ala | — | gly—pro |
| CBZ—gly—pro—leu—gly—pro | + | pro—leu |
| Benzoyl-arginine ethyl ester | — | — |
| CBZ—gly—p-nitro-phenyl ester | — | — |
| Tosyl-arginine ethyl ester | — | — |
| Benzoyl-arginine-p-nitroanilide | — | — |
| Benzoyl-phe—val—arg—p-nitro-anilide | + | amide |
| CBZ—gly—pro—arg—p-nitroanilide | — | — |

TABLE 6
LYSIS OF MICROORGANISMS AT 75° C. BY CALDOLYSIN (20 μg ml$^{-1}$, 0.1 M CH$_3$COONa, pH 7.5)

| Microorganism | ATCC Numbers | Gram reaction a | Complete lysis | Partial lysis | No lysis |
|---|---|---|---|---|---|
| Arthrobacter globiformis | 8907 | + | | | + |
| Arthrobacter | — | + | | | + |
| Bacillus cereus | 9373 | + | | + | |
| Bacillus megaterium | 9376 | + | | | + |
| Bacillus circulans | 9374 | + | | + | |
| Micrococcus luteus | — | + | | | + |
| Micrococcus lysodeikticus | — | + | | + | |
| Saccharomyces cerevisiae | — | + | | | + |
| Sarcina lutea | 196 | + | | | + |
| Sporeformer (unidentified Bacillus) | — | + | | | + |
| Staphylococcus aureus | 6571 | + | | | + |
| Streptomyces griseus | 8136 | + | | + | |
| Agrobacterium tumefaciens | 15955 | — | | | + |
| Alcaligenes faecilis | 8156 | — | + | | |
| Alcaligenes viscolactis | 8154 | — | + | | |
| Citrobacter freundii | — | — | + | | |
| Cytophaga johnsonae C$_4$ | — | — | | | + |
| Escherichia coli B | 11303 | — | + | | |
| Escherichia coli K$_{12}$ | — | — | + | | |
| Escherichia coli K$_{12}$Hfr | — | — | + | | |
| Escherichia coli W | — | — | + | | |
| Enterobacter aerogenes | — | — | + | | |
| Enterobacter cloacae | — | — | + | | |
| Klebsiella pneumoniae | 418 | — | + | | |
| Proteus vulgaris | 67 | — | + | | |
| Pseudomonas aerogenes | — | — | + | | |
| Salmonella typhimurium | — | — | + | | |
| Serratia marcescens | 1377 | — | + | | |
| Shigella flexneri | — | — | + | | |

TABLE 6-continued

LYSIS OF MICROORGANISMS AT 75° C. BY
CALDOLYSIN (20 μg ml$^{-1}$, 0.1 M
CH$_3$COONa, pH 7.5)

| Microorganism | ATCC Numbers | Gram reaction a | Complete lysis | Partial lysis | No lysis |
|---|---|---|---|---|---|
| Shigella sonnei | — | — | + | | | a. Gram reactions quoted from Bergeys Manual of Determinative Bacteriology (1974), 8th edition, (Buchanan R. E. and Gibbons N. E., eds.) Williams & Wilkins Ltd.

TABLE 7

| ENZYME NAME | SOURCE | HALF-LIFE | TEMPERATURE |
|---|---|---|---|
| THERMOLYSIN | BACILLUS THERMOPROTEOLYTICUS | 1 hr | 80° C. |
| THERMOMYCOLASE | MALBRANCHIA PULCHELLA | 1.8 hr | 73° C. |
| AMINOPEPTIDASE 1 | BACILLUS STEAROTHERMOPHILUS | 0.3 hr | 80° C. |
| PROTEASE | BACILLUS CALDOLYTICUS | >8.3 hr | 80° C. |
| CALDOLYSIN | THERMUS T-351 | >24.0 hr* | 75° C. |
| CALDOLYSIN | THERMUS T-351 | 30 hr* | 80° C. |
| CALDOLYSIN | THERMUS T-351 | 5 hr* | 85° C. |
| CALDOLYSIN | THERMUS T-351 | 1 hr* | 90° C. |
| CALDOLYSIN | THERMUS T-351 | ½ hr* | 95° C. |

*Assay conditions 0.5% casein, 75° C., 30 minutes, pH 8.1
Incubation conditions pH 8 buffer + 10 mM Ca$^{2+}$, temperature ± 0.5° C.

(3) Stabilising Effect of Divalent Cations

Table 8 shows influence of metal ions on the stability of CALDOLYSIN at 85° C. (12 μg ml$^{-1}$ enzyme, pH 8.1 Tris acetic acid, I=0.3 M 1$^{-1}$). CALDOLYSIN was dialysed in the presence of 1.0 mM EDTA to remove any metal ion cofactors. Standard metal ion solutions were added to aliquots of the "apoenzyme" to give 10 mM concentration, after which the thermostability of the enzyme was determined.

TABLE 8

| Metal ion | Half-life (minutes) |
|---|---|
| Calcium | est. 340 |
| Zinc | 144 |
| Strontium | 155 |
| Magnesium | 86 |
| Cobalt | 60 |
| Barium | 43 |
| Copper | 21 |
| None | est. 5–10 |

(4) Stability to Denaturing Agents

CALDOLYSIN has been found to be stable and active in the presence of a variety of denaturing agents as shown in Table 9.

TABLE 9

Stability of CALDOLYSIN in the present of denaturing agents.

| Denaturing agent | Half life at 18° C. | Half life at 75° C. |
|---|---|---|
| 1% SDS | >>13 hours | >5 hours |
| 8M Urea | >>67 hours | 53 minutes |
| 0.8M Urea | >>13 hours | 148 minutes |
| 6M Guanidine HCl | >>31 hours | 59 minutes |
| 1% Triton X100 | — | >>60 minutes |
| 1% Tween 80 | — | >>60 minutes |

(5) Other

CALDOLYSIN is stable to concentration by lyophilisation (freeze-drying) and rotary evaporation (reduced pressure at 37° C.) as shown in Table 10.

TABLE 10

| Method of Concentration | Concentration Factor | % Specific Activity Loss |
|---|---|---|
| Lyophilisation | 7 | 7.2% |
| Rotary Evaporation | 20 | <5.0% |

D. pH/Activity Relationships

Optimum pH for activity on azocasein occurs at 8.5±0.5. (at 75° C.). At pH 6.0–pH 9.5, more than 80% of optimal activity is retained.

E. Temperature/Activity Relationships

Below 40° C. enzyme activity is low (less than 6% of activity at 80° C.). Activity rises almost linearly between 45° C. and 80° C.

NB: Although % activity is low at normal temperatures (20°–40° C.), sufficient activity for effective proteolysis can be obtained simply by using larger quantities of enzyme. However, its usefulness is clearly maximal at 65° C.–85° C.

EXAMPLE 4

THERMUS T-351 Growth and CALDOLYSIN PRODUCTION

Optimum production of CALDOLYSIN was achieved when THERMUS T-351 was grown on peptone media containing Allen's salts at peptone concentrations of 0.6% to 1%, (Cell division time ~2 hours). Concentrations of peptones greater than 1% inhibited production. THERMUS T-351 grew poorly on salts/casein or salts/albumin media, and excreted little protease. However, yields of extracellular protease could be increased significantly by addition of protein substrates to 0.6% peptone media. At 75° C., optimum yield of CALDOLYSIN occurred within 18 hours (19% inoculum, aeration=media vol./min.).

Yield: 0.12 PU/ml culture medium: where 1 PU=1 mg tyr released/min at 75° C.; substrate=0.5% casein.

EXAMPLE 5

Immobilisation of CALDOLYSIN to Glass Beads

CALDOLYSIN was immobilised on non-porous glass beads by the silane glutaraldehyde-coupling method described by Stolzenbach & Kaplan [(1976). Methods in Enzymology 44, 926]. 10 g of glass beads (Corning glass, 100 mesh) was washed in an excess of 5% HNO$_3$ at 100° C. for 30 minutes. The acid-washed glass was filtered and rinsed, then added to a 10% aqueous solution of γ-aminopropyl triethoxysilane (adjusted to pH 3.5 with HNO$_3$). The suspension was incubated at 75° C. for approximately three hours to permit silanization to occur. After filtering, the silanized glass was added to a 20 ml volume of 5% glutaraldehyde in 0.01 M, pH 7, phosphate buffer. This was reacted in vacuo for two hours at room temperature, and finally washed exhaustively with distilled water.

17 ml of a solution of CALDOLYSIN (25 μg ml$^{-1}$) of known activity was added to the prepared ceramic substrate. The suspension was stirred at room temperature for 18 hours to complete glutaraldehyde crosslinking. The immobilised enzyme was subsequently filtered, washed with 100 ml H$_2$O, 100 ml 1 M NaCl, and a further 500 ml H$_2$O. The filtrate and washings were assayed by the Kunitz method.

The immobilised complex was assayed by a modification of the Kunitz method. 14 mg samples of the enzyme-bead complex were placed in reaction tubes, mixed with 2 ml of 0.5% casein substrate, and incubated at 75° C. with continual shaking. The proteolytic activities of the original enzyme solution, the immobilised preparation, and the washings (non-immobilised enzyme) were calculated (Table 11).

TABLE 11

| Activity of Glass-bead-immobilised CALDOLYSIN | Enzyme activity (PU) |
|---|---|
| Total enzyme activity of original solution | 25.4 |
| Total enzyme activity not bound to glass beads | 0.6 |
| Total activity of ceramic-bound enzyme | 0.2 |
| Recovery of activity in immobilised = state | 1% |

It is concluded that CALDOLYSIN was either inactivated during the attempt to cross-link it to the silanized glass, or was bound in such an orientation that steric hindrance prevented access of the protein substrate to the catalytic site.

EXAMPLE 6

Immobilisation of CALDOLYSIN to Sepharose 4B

Sepharose 4B (Pharmacia) was activated with cyanogen bromide as described by Fujiwara & Tsuru [(1977) *International Journal of Peptide and Protein Research*, 9, 18]. During activation, the Sepharose suspension was maintained at 25° C., and at pH 10 to 11 by dropwise addition of 4 N NaOH. The activated gel was washed and stored at 4° C.

15 ml of a CALDOLSYIN solution (25 μg ml$^{-1}$ in 0.1 M CH$_3$COONa, pH 7.2) was adjusted to pH 9.7 and added to 40 ml of settled activated Sepharose 4B. The mixture was incubated at 4° C. for 72 hours. Subsequently, the CALDOLYSIN-Sepharose complex was filtered and washed with distilled water. Assay results for the free enzyme, immobilised enzyme and gel washings are presented in Table 12.

TABLE 12

| Activity of Sepharose 4B-immobilised CALDOLYSIN | Enzyme activity (PU) |
|---|---|
| Total activity of free enzyme solution | 17.0 |
| Total activity not bound to Sepharose | 0.7 |
| Total activity of Sepharose-bound enzyme | 12.0 |
| Recovery of activity in immobilised state = | 73% |

EXAMPLE 7

Immobilisation of CALDOLYSIN to Carboxymethylcellulose

The Curtius azide method, first described by Michael & Ewers [(1949) *Makromolekular Chemie* 3, 200] modified by Mitz & Summaria [(1961) *Nature* 189, 576] and detailed by Crook et al. [(1970) *Methods in Enzymology* 19, 963] and Lilly [(1976) *Methods in Enzymology* 44, 46] was used to immobilise CALDOLYSIN to CM-cellulose. 5 g of CM-cellulose (Pharmacia) was treated with methanol in acid, hydrazine hydrochloride, and sodium nitrite in acid, as described in the papers cited above.

To the activated cellulose was added 77 ml of CALDOLYSIN (61.5 μg ml$^{-1}$ in pH 9.2 buffer). The substrate-enzyme coupling reaction was accompanied by a decrease in pH, which was readjusted to 8.7 by addition of saturated sodium borate solution during the 60 minute duration of reaction. The complex was subsequently washed with aliquots of distilled water, NaCl, acetic acid, and sodium bicarbonate solutions. The immobilised complex and all solutions were assayed as previously described. Activity data are presented in Table 13.

TABLE 13

| Activity of CALDOLYSIN immobilised to CM-cellulose | Enzyme activity (PU) |
|---|---|
| Total activity of free enzyme solution | 239 |
| Total activity not bound to CM-cellulose (washings) | 29 |
| Total activity of CM-cellulose-immobilised CALDOLYSIN | 66 |
| Recovery of activity in immobilised = state | 31% |

EXAMPLE 8

Comparative data for free and immobilised CALDOLYSIN

It has been shown in examples 5 to 7 that the immobilisation of CALDOLYSIN to various insoluble substrates occurs with considerable differences in the recovery of active immobilised enzyme (i.e. 1% for glass beads, 31% for CM-cellulose, and 73% for Sepharose 4B). This may be due to loss of activity by denaturation, or differences in inhibition due to the site of the enzyme-matrix covalent linkage.

The activity retained after immobilisation of CALDOLYSIN to Sepharose (73%) was high when compared to other published data. In binding a range of proteases to Dowex MWA-1 anion exchange resin, Ohmiya et al. [(1978) *Biotechnology and Bioengineering* 20, 1], found activity yields ranging from 3% to 39%. Mason et al. [(1975) *Biotechnology and Bioengineering* 17, 1019] obtained activity yields of 41.4% and 57.7% on coupling *B. subtilis* neutral protease to glass by the azo- and glutaraldehyde methods, respectively.

A range of characteristics of the immobilised CALDOLYSIN preparations, including thermostabilities, pH activity profiles, and Michaelis-Menten kinetics, were compared with those of the free enzyme. Since the residual activity of the glass-bead immobilised enzyme was extremely low, no further study of this complex was carried out.

The thermostabilities of the immobilised CALDOLYSIN preparations were determined at different temperatures and calcium concentrations. Volumes of immobilised enzyme were suspended in 0.1 M Tris acetic acid buffer, pH 8.1, containing known concentrations of calcium. The suspensions were incubated at the desired temperature, and aliquots removed at intervals for assay after agitation of the suspension to ensure homogeneity. Immobilised apoenzyme suspensions were obtained by eluting the insoluble complex (held in a Pharmacia K12 glass column) with 10 mm EDTA for several hours, and final washing with distilled water. (The term "apoenzyme" is subject to the conditions discussed previously: it is possible that in the immobilised state, tightly bound calcium ions might not be removed by such treatment). Thermostability data is presented in Table 14.

TABLE 14

A comparison of the thermostabilities of free and immobilised CALDOLYSIN

| Enzyme status | Calcium status | $Ca^{2+}$ (mM) | Half-life (minutes) at T° C. | | |
|---|---|---|---|---|---|
| | | | 85 | 90 | 95 |
| Free | Holo | 10 | 360 | 60 | 28 |
| Sepharose-bound | Holo | 10 | 1060 | 165 | 125 |
| CM-cellulose-bound | Holo | 10 | — | 110 | — |
| Free | Apo | 0 | — | >6 | — |
| Sepharose-bound | Apo | 0 | — | 28 | — |
| Free | Holo | 0 | — | approx.15 | — |
| Sepharose-bound | Holo | 0 | — | 64 | — |

The immobilisation of CALDOLYSIN on Sepharose results in an increase in thermostability of 3 to 4-fold over a number of different temperatures and conditions, while a thermostability increase of approximately 2-fold results from covalent linkage to CM-cellulose. The decrease in stability of the holo-enzyme Sepharose complex when incubated in a calcium-free buffer suggests that the stabilisation by high calcium concentrations is as significant a factor in the immobilised state as in the free enzyme, while the decreased stability of the Sepharose-immobilised enzyme after EDTA treatment ("apoenzyme") indicates that immobilisation does not prevent the removal of at least some of the calcium-conferred stabilisation.

A sample of THERMUS T-351 has been deposited with the American Type Culture Collection, 12301 Parklawn Drive, Rockville, Md. 20852, United States of America under number 31,674.

EXAMPLE 9

Stability of CALDOLYSIN at varying concentrations of Ca++

The half-lives of CALDOLYSIN in the presence of different concentrations of calcium ions is presented in Table 15. The CALDOLYSIN and ion solutions were prepared as in Example 3 (C) (3) above.

TABLE 15

| $Ca^{++}$ Concentration mM | Half life min. |
|---|---|
| 0 | <10 |
| 0.1 | 15 |
| 0.5 | 22 |
| 1 | 38 |
| 5 | 225 |
| 10 | ~360 |
| 50 | 600 |
| 100 | 780 |

TABLE 15-continued

| $Ca^{++}$ Concentration mM | Half life min. |
|---|---|
| 500 | 780 |

What is claimed is:

1. A culture of THERMUS AQUATICUS (VARIETY T-351), ATCC No. 31,674, in substantially biologically pure form.

2. A process for isolating THERMUS AQUATICUS (VARIETY T-351), ATCC No. 31,674 in a substantially biologically pure form, which process comprises:
    (a) isolating a sample of solution from a hot pool (at 79°±4° C.) low in sulphide at pH 7.8 containing said THERMUS AQUATICUS (VARIETY T-351),
    (b) preparing a culture from said sample with a culture medium and maintaining said culture at at temperature of 65° C. to 85° C. and a pH between 7.2 and 8.2 for a culturing period sufficient to produce an adequate yield, and
    (c) recovering the THERMUS AQUATICUS (VARIETY T-351) from said culture during the late log phase thereof.

3. A process according to claim 2, wherein said hot pool is Hot Pool Number 351 as marked on the map of "Whakarewarewa Hot Springs", 1:2000, First Edition by New Zealand Geological Survey (Bibliographic Reference-LLOYD, E. F. 1974 Geology of Whakarewarewa Hot Springs, DSIR Information Series Number 104 DSIR, Wellington, New Zealand).

4. A process according to claim 2 or 3 wherein said step (b) comprises repeated subculturing of said sample in a half strength nutrient broth at pH 8.0, and broth volume being substantially ten times the sample volume, at 75° C.

5. A process according to claim 4 wherein said culture medium comprises a liquid containing Allen's salts with 0.1 to 0.3 percent w/v yeast extract and 0.1 to 3 percent w/v trypticase at a pH of 7.5.

6. A process according to claim 5 wherein said pH is raised to 8.2 and the medium is autoclaved prior to inoculation with said culture.

7. A process according to claim 5, wherein said THERMUS AQUATICUS (VARIETY T-351) is recovered for use by harvesting at the end of said culturing period.

8. A process according to claim 5, wherein said culture prepared in step (b) is used to inoculate a fermentation process.

9. A process for preparing a culture of THERMUS AQUATICUS (VARIETY T-351), ATCC No. 31,674, said process comprising:
    (a) isolating a sample of solution from a hot pool (79°±4° C.) low in sulphide at pH 7.8 containing said THERMUS AQUATICUS (VARIETY T-351),
    (b) preparing a culture from said sample with a culture medium and maintaining said culture at a temperature of 65° C. to 85° C. and pH between 7.2 and 8.2 for a culturing period sufficient to produce an adequate yield of said culture.

10. A process according to claim 9, wherein said step (b) comprises repeated subculturing of said sample in a half strength nutrient broth at pH 8.0, the broth volume being substantially ten times the sample volume, at 75° C.

11. A process according to claim 10, wherein said culture medium comprises a liquid containing Allen's salts with 0.1 to 0.3% w/v yeast extract and 0.1 to 3% w/v trypticase at a pH of 7.5.

12. A process according to claim 11, wherein said culture prepared in step (b) is used to inoculate a fermentation process.

13. A process according to claim 11, wherein said THERMUS AQUATICUS (VARIETY T-351) is recovered for use by harvesting at the end of said culturing period.

14. A process according to claim 2 or 9, wherein said culture is maintained at a temperature of 75° C.